United States Patent
Fuchiwaki et al.

(10) Patent No.: US 7,726,210 B2
(45) Date of Patent: Jun. 1, 2010

(54) SAMPLE MOVEMENT CONTROL UNIT, SAMPLE MOVEMENT PARAMETERS ACQUISITION METHOD, AND SAMPLE MOVEMENT CONTROL METHOD

(75) Inventors: Ohmi Fuchiwaki, Chofu (JP); Naoto Chiba, Chofu (JP); Hisayuki Aoyama, Chofu (JP)

(73) Assignee: The University of Electro-Communications, Tokyo (JP)

( * ) Notice: Subject to any disclaimer, the term of this patent is extended or adjusted under 35 U.S.C. 154(b) by 414 days.

(21) Appl. No.: 11/573,871

(22) PCT Filed: Feb. 18, 2005

(86) PCT No.: PCT/JP2005/002584

§ 371 (c)(1),
(2), (4) Date: Sep. 27, 2007

(87) PCT Pub. No.: WO2006/018913

PCT Pub. Date: Feb. 23, 2006

(65) Prior Publication Data

US 2008/0257074 A1    Oct. 23, 2008

(30) Foreign Application Priority Data

Aug. 19, 2004    (JP) .............................. 2004-239482

(51) Int. Cl.
*G01N 1/22* (2006.01)
(52) U.S. Cl. .................................. 73/863.01
(58) Field of Classification Search ............... 73/863.01

See application file for complete search history.

(56) References Cited

U.S. PATENT DOCUMENTS 6,945,129 B2 * 9/2005 Escal ....................... 73/864.24
2003/0077815 A1 4/2003 Omata

FOREIGN PATENT DOCUMENTS

JP        2001239500 A      9/2001

OTHER PUBLICATIONS

Inoue, Y., et al., "An Ultra Precision Production System Organized by Multiple Micro Robots," Seimitsu Kogakkai Taikai Gakujutsu Koenkai Koen Ronbunshu, vol. 2004, Shunki (CD-ROM), Mar. 1, 2004, p. MO1.
Chiba, N., et al., "An Ultra Precision Production System Organized by Multiple Micro Robots," Seimitsu Kogakkai Taikai Gakujutsu Koenkai Koen Ronbunshu, vol. 2004, Shuki (CD-ROM), Sep. 1, 2004, p. LO3.

* cited by examiner

*Primary Examiner*—Hezron Williams
*Assistant Examiner*—Rodney T Frank
(74) *Attorney, Agent, or Firm*—Christensen O'Connor Johnson Kindness PLLC

(57) ABSTRACT

There is provided a device and a method capable of simply manipulating a sample, without the need for an expensive device.

A device of the present invention comprises a pipette 4, and vibration section 5, a control section 7 and a storage section 8. At least part of the pipette 4 will be disposed within a liquid 2. The control section 5 causes the pipette 4 to vibrate. The control section 7 supplies vibration signals to the vibration section 5. The storage section 8 stores parameters for generating vibration signals. These parameters include information for generating a first vibrating wave causing a wave motion for drawing a particular sample 3 being within a specified distance from a tip of the pipette 4 to occur within a liquid 2, and information for generating a second vibrating wave causing a wave motion for rotating the drawn in sample 3 to occur. The information for generating the first standing wave and the information for generating the second standing wave are, for example, amplitude and frequency of vibration.

8 Claims, 7 Drawing Sheets

FIG.3
(a)
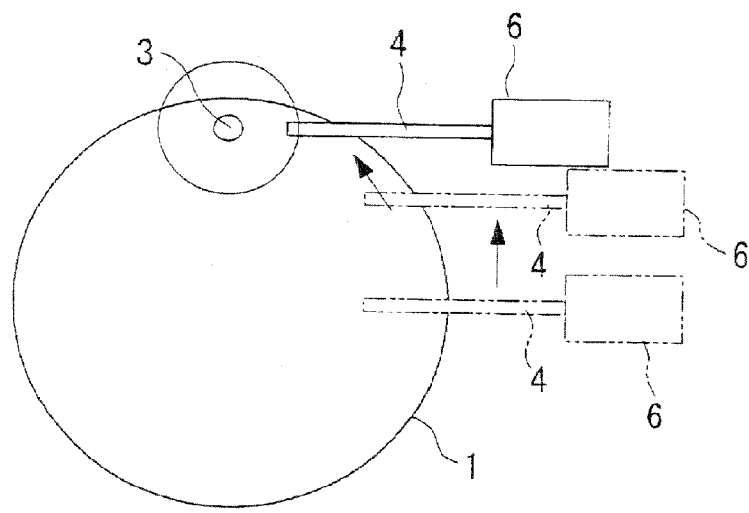
(b)
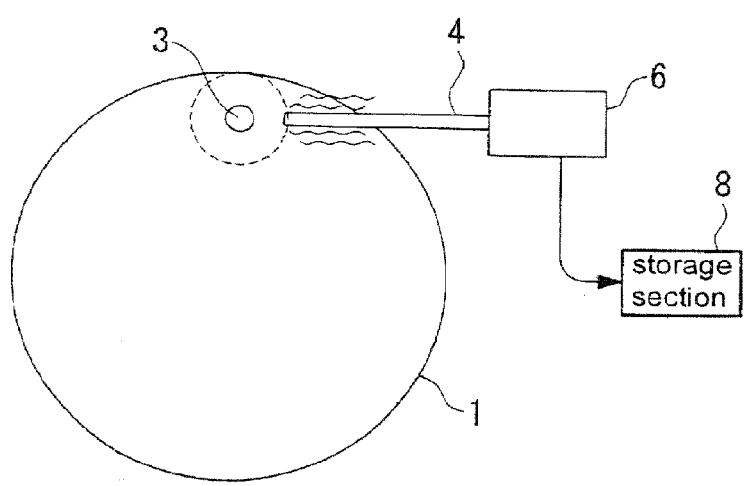
(c)
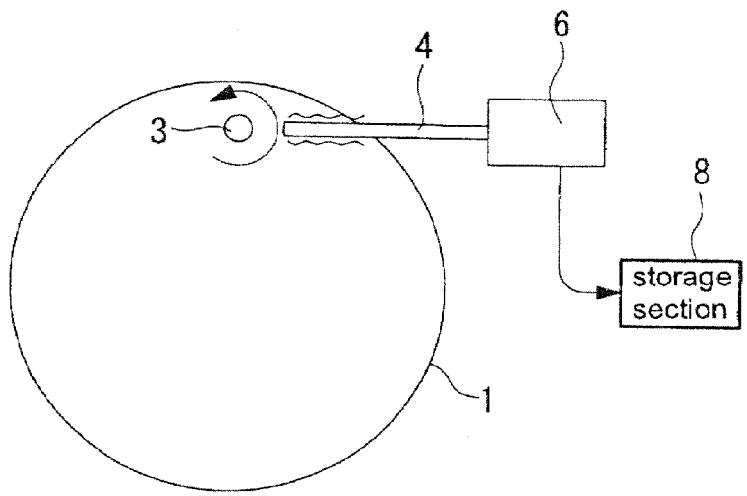

FIG.9
(A)
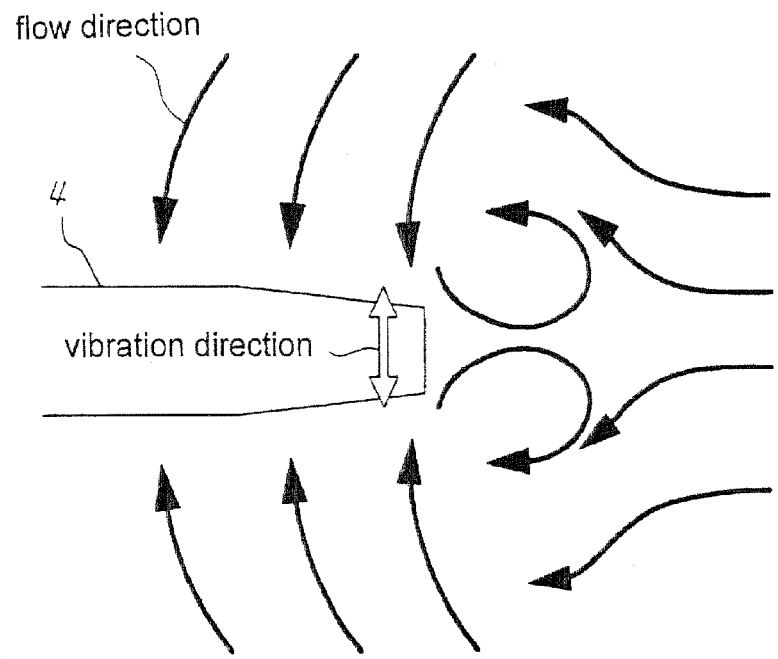
(B)
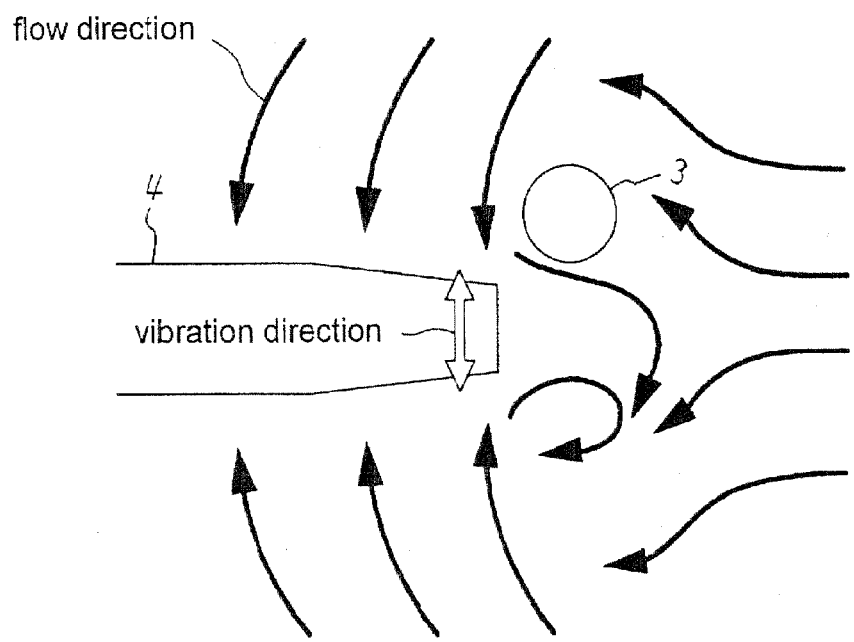

SAMPLE MOVEMENT CONTROL UNIT, SAMPLE MOVEMENT PARAMETERS ACQUISITION METHOD, AND SAMPLE MOVEMENT CONTROL METHOD

TECHNICAL FIELD

The present invention relates to technology for controlling position and attitude of a sample such as a cell.

BACKGROUND ART

For example, in a cell operation such as rotation and positioning of an ovum in microfertilization or microinsemination, controlling of position and attitude of a cell, being a small sample, is important. As an operation method for a small sample, a method using a manipulator, a method using an alternating electric field, a method using laser light, and a method using vibration are known. Outlines of these methods will be described in the following.

(Method Using a Manipulator)

As a method using a manipulator, for example, a holding pipette is physically hooked and turned, or inner pressure of a holding pipette is varied to suck in or expel, to incidentally vary the attitude of a sample. However, this type of method requires skill and takes a lot of time for a beginner, and is known to be inefficient. With this method, therefore, there is the disadvantage that a system for assisting adjustment of physical attitude and position, or alternatively a system for automatic injection, are required.

(Method Using an Alternating Electric Field)

As a method using an alternating electrical field, attitude and position of a dielectric such as a cell are controlled by, for example, placing a plurality of electrodes inside a dish, and applying an alternating electrical field. With this method, it is necessary to take into consideration damage inflicted on the cell etc. by application of the electric field. Also, arranging a sample with good accuracy close to a glass pipette is difficult, and it is necessary to bring the glass pipette close to the sample. Therefore, the method using an alternating electric field is currently only used in extremely limited operations.

There have also been reports of a method used with organic sample microscopic operations, where electrodes are attached to a holding pipette and an injection pipette, and an alternating electric field generated between the two glass pipettes to carry out rotation of the sample (refer to patent publication 1, below). However, with this procedure there is a problem that a new operation is required to attach electrodes to the glass pipettes.

(Method Using Laser Light)

As a method using laser light, laser light is condensed by a lens, and a transparent sample is manipulated. With this method, by increasing output of the laser light used, it is also possible to perform processing of a few μm or less. This method can carry out non-contact sample manipulation and processing at the same time, but since laser light is used it is not possible to use directly in normal microscopic manipulations, and it is necessary to newly install a dedicated structure. There is therefore the drawback with implementation of this method that is demands extremely high cost.

(Method Using Vibration)

As a method using vibration, a rod-shaped vibrator such as a glass pipette is vibrated, to generate at least one standing wave in the vibrator (refer to patent publication 2 below). With this method, a sample is trapped at a node portion of a standing wave generated in the vibrator, and the sample is rotated.

However, the position of the standing wave node is more or less fixed according to the vibration mode. For this reason, with this method the position where it is possible to manipulate a sample is limited by the vibration mode. In particular, with this method manipulation of a sample at the tip end of a pipette is considered difficult. This is because it considered that a node is not generated at the pipette tip.

Besides the methods described above, there have also been reports of using ultrasound and using thermosetting resin in manipulation methods for microscopic samples, but in practical terms there are still many unresolved problems.

Patent Publication 1
Japanese Patent Laid-open No. 2001-239500
Patent Publication 2
International Patent Publication No. WO01/072951

DISCLOSURE OF THE INVENTION

The present invention has been conceived in view of the above-described situation. An object of the present invention is to provide a device capable of simply controlling movement of a sample, and a method of simply controlling movement of a sample, without the need for an expensive device.

A sample movement control device disclosed herein is provided with a pipette, a vibration section, a control section and a storage section. At least part of the pipette is to be disposed within a liquid. The vibrating section is constructed to vibrate the pipette. The control section is constructed to supply vibration signals, for causing the pipette to vibrate, to the vibration section. The storage section is constructed to store parameters for generating the vibration signals. The parameters include information for generating a first vibrating wave causing a wave motion for drawing a sample being within a specified distance from the pipette to occur within the liquid, and information for generating a second vibrating wave causing a wave motion for rotating the drawn in sample to occur.

Information for generating the first vibrating wave and information for generating the second vibrating wave may contain at least information on amplitude and frequency of vibration.

A method of according to the invention for acquiring parameters for sample movement may comprise the following steps:

(1) a step of storing pipette position and sample position in a storage section;

(2) a step of, after step (1), determining, using a control section, whether or not a distance between the pipette and the sample is within a specified range;

(3) a step of storing, when the distance between the pipette and the sample is within a specified distance, a parameter for causing the pipette to vibrate so as to reproduce a first vibrating wave at the time the sample has moved close to the pipette; and (4) a step of, after step (3), storing a parameter for causing the pipette to vibrate and reproducing a second vibrating wave at the time the sample has been rotated.

A sample movement control method according to the invention may comprise the following steps:

(1) a step of storing pipette position and sample position in a storage section;

(2) a step of, after step (1), determining, using a control section, whether or not a distance between the pipette and the sample is within a specified range;

(3) a step of generating a first vibrating wave based on a parameter stored in a storage section when the distance between the pipette and the sample is within a specified distance and causing the sample to move close to the pipette; and (4) a step of, after step (3), generating a second vibrating wave based on a parameter stored in the storage section, to cause the pipette to vibrate, and causing the sample to rotate.

In the invention, a piezoelectric element may be used as the vibrating section.

In the sample movement control device, the pipette may be attached to a vibration section, and the vibration section may be attached to a robot for moving in at least the X and Y directions.

A method according to the invention for acquiring parameters for sample movement may comprise the following steps:

(1) a step of determining, using a control section, whether or not a distance between the pipette and the sample is within a specified range;

(2) a step of storing, when the distance between the pipette and the sample is within a specified distance, a parameter for causing the pipette to vibrate so as to reproduce a first vibrating wave at the time the sample has moved close to the pipette; and (3) a step of, after step (2), storing a parameter for causing the pipette to vibrate so as to reproduce a second vibrating wave at the time the sample has been rotated.

A sample movement control method according to the invention may comprise the following steps:

(1) a step of determining, using a control section, whether or not a distance between the pipette and the sample is within a specified range;

(2) a step of generating a first vibrating wave based on a parameter stored in a storage section when the distance between the pipette and the sample is within a specified distance to cause the pipette to vibrate and causing the sample to move close to the pipette; and (3) a step of, after step (2), generating a second vibrating wave based on a parameter stored in the storage section, to cause the pipette to vibrate, and causing the sample to rotate.

According to the present invention it is possible to provide a device capable of simply controlling movement of a sample, and a method of simply controlling movement of a sample, without the need for an expensive device.

BRIEF DESCRIPTION OF THE DRAWINGS

FIG. 3 is an explanatory drawing for describing operation of the device of FIG. 1 in acquiring parameters for sample manipulation.

FIG. 9 is an explanatory drawing for describing flow of liquid accompanying vibration of the pipette. FIG. 9(A) shows flow of the liquid in a state where the pipette is being vibrated in order to bring the sample closer. FIG. 9(B) shows flow of the liquid in a state immediately before the sample is close to a pipette and about to be rotated.

PREFERRED MODE OF EMBODYING THE INVENTION

Structure of the Embodiment

One embodiment of the present invention will be described below with reference to the attached drawings. First, the basic structure of a sample movement control device of this embodiment will be described based on FIG. 1. As a prerequisite, this device is for manipulating a sample 3 placed in a liquid 2 inside a container 1. The sample 3 is a cell such as an ovum, for example, but can be another microscopic sample. The size of the sample is not particularly limited.

Figure 1:
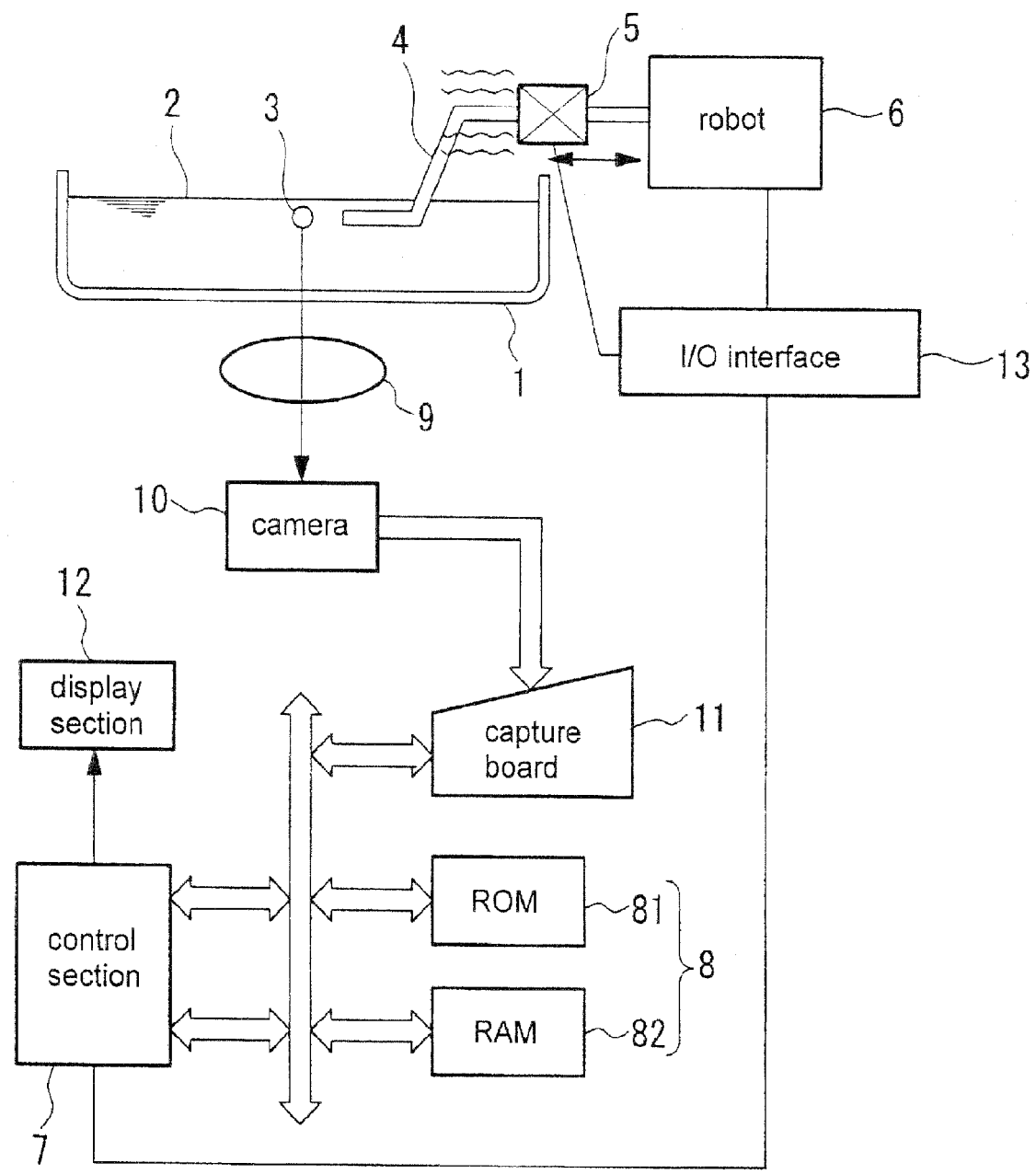
FIG. 1 is a block diagram for describing the conceptual structure of a sample movement control device of one embodiment of the present invention.

The device of this embodiment basically comprises a pipette 4, a vibration section 5, a robot 6, a control section 7, a storage section 8, a lens 9, a camera 10, a capture board 11, a display section 12, and an I/O interface 13 (refer to FIG. 1).

A tip of the pipette 4 is placed in the liquid 2 (refer to FIG. 1). In this embodiment it is possible to use a conventionally used holding pipette made of glass as the pipette 4. However, the material and shape of the pipette 4 are not particularly limited.

The vibration section 5 is attached to a base section of the pipette 4. A piezoelectric element, for example, can be used as the vibration section 5. It is possible to cause the piezoelectric element to vibrate by varying a voltage applied to the piezoelectric element. It is also possible, however, to have the vibration section 5 built-in to the robot 6.

The robot 6 is constructed so as to be capable of moving the pipette 4 to an arbitrary position. It is preferable for the robot 6 to be capable of being self-propelled, and to be small, from the point of view of improving operability. Such a robot is disclosed in Japanese patent laid-open No. 2002-254398, proposed by the present inventors. With the robot disclosed in this publication, movement is possible in three independent degrees of freedom in the XY θ directions. With this robot it is also possible to use the piezoelectric element for movement for application to the vibration section 5, making further size reduction possible. However, it is also acceptable if the robot 6 is not self-propelled. It is also possible for the robot 6 to be mounted on a movable table, and to move in accordance with movement of the table.

The control section 7 supplies vibration signals to the vibration section 5. With this embodiment, the control section 7 is constituted by a CPU. A method of supplying control signals using the control section 7 is exemplified in operation of this embodiment.

The storage section 8 is constructed to store parameters for generating vibration signals. The storage section 8 is constructed from ROM 81 and RAM 82.

Computer programs for manipulation of the device and parameters for use in operation of the device to be described later are stored in the ROM 81. Parameters and data acquired by the device of this embodiment are stored in the RAM 82.

Parameters for generating vibration signals contain at least two items of information. One item of information is information for generating a first vibrating wave for causing wave motion, for drawing a sample 3 that is within a specified distance of the tip of the pipette 4 towards the tip, to occur in the liquid 2. The other item of information is information for generating a second vibrating wave to cause wave motion for rotating the drawn in sample 3. As information for generating vibrating waves there is, for example, amplitude and frequency. It is also possible to further include information about vibration direction (for example, XYZ directions). However, information included in parameters is not particularly limited. For example, it is preferable to include in the parameters information regarding distance from the surface of the liquid 2 to the pipette 4, distance from the pipette 4 to the bottom of the container 1, material and shape of the pipette 4, material and shape of the bottom of the container 1, viscosity, temperature and density of the liquid 2, etc., as required.

The lens 9 is mounted between the camera 10 and the sample 3, and is configured so as to acquire an image of the sample 3 with the camera 10. Naturally it is possible to omit the lens 9 as long as a required image can be obtained using the camera 10 only.

The camera 10 is disposed so as to be capable of acquiring an image of the sample 3 via the lens 9, as described previously. It is possible to use a CCD camera or CMOS camera, for example, as the camera 10, but the type of camera is not particularly limited. As well as a visible light camera, it is also possible to use any type of camera such as an infra-red camera or rangefinder, depending on the application.

The capture board 11 subjects an image acquired by the camera 10 to A/D conversion. Converted data is stored in the RAM 82 of the storage section 8 based on commands from the control section 7.

The display section 12 is configured to perform display appropriate for the user. As the display section 12 there are, for example, a display or a printer.

The I/O interface 13 performs an input output interface function between the control section 7, and, the robot 6 and the vibration section 5.

(Method of Acquiring Parameters, Using the Device of this Embodiment)

Next, an example of a method for acquiring parameters for sample movement, using the device of this embodiment, will be described with reference to the flowchart of FIG. 2. This acquisition method is executed based on data and parameters stored in the ROM 81 of the storage section 8. Data and parameters acquired by this method are stored in the RAM 82

Figure 2:
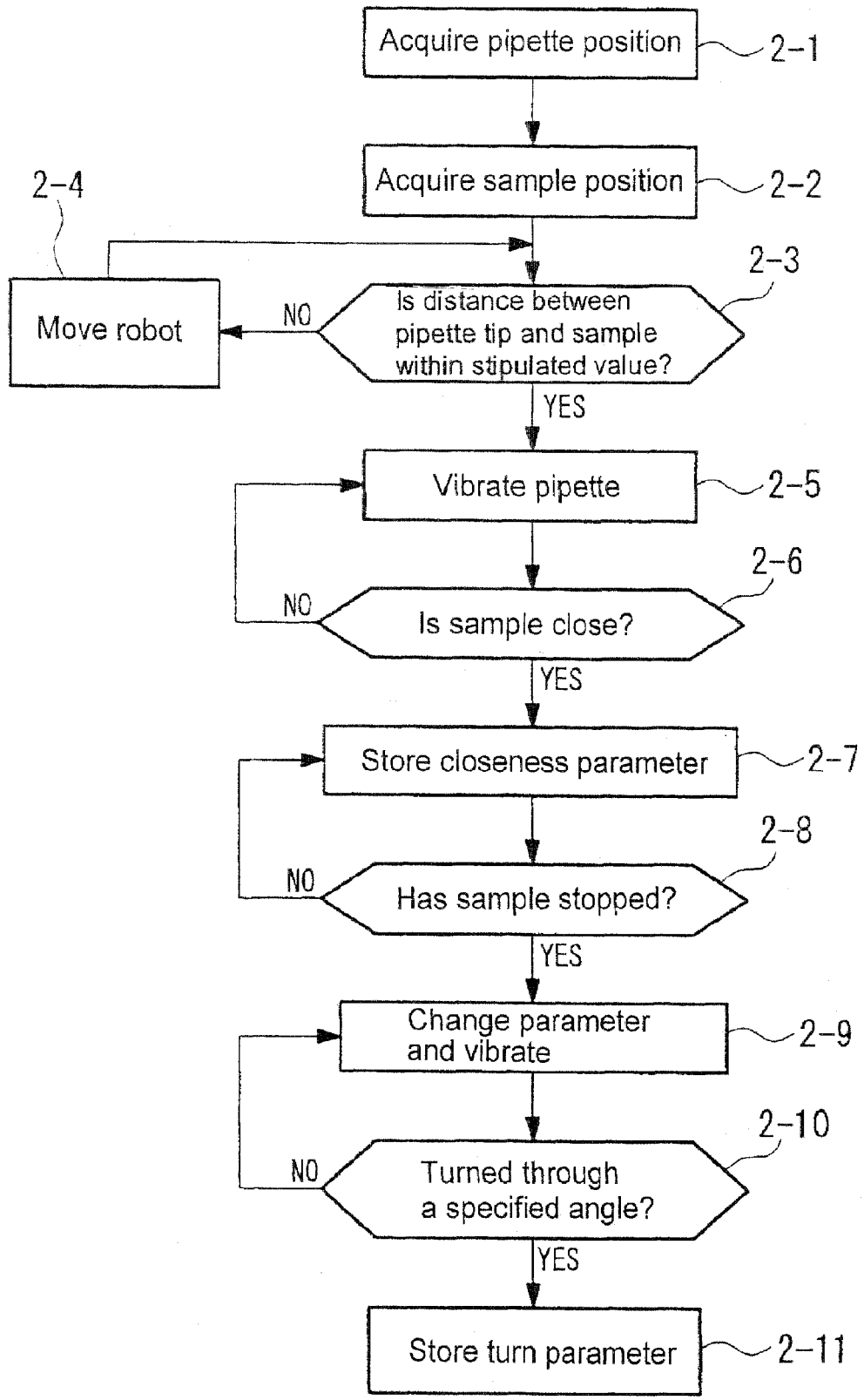
FIG. 2 is a flowchart for describing a method of acquiring parameters for sample manipulation, using the device of FIG. 1.

(Steps 2-1 and 2-2 in FIG. 2)

First, an image including the tip of the pipette 4 and the sample 3 is acquired by the camera 10. Then, this image is analyzed, positions of the pipette tip and the sample are analyzed by the control section 7, and the results are stored in the RAM 82 of the storage section 8.

(Step 2-3 in FIG. 2)

Next, it is determined by the control section 7 whether or not the distance between the tip of the pipette 4 and the sample 3 is within a control value. The control value is stored in advance in the ROM 81.

(Step 2-4 in FIG. 2)

In the event that the distance between the tip of the pipette 4 and the sample 3 is in excess of the control value, the robot 6 is moved in the direction of the sample 3 (refer to FIG. 3(*a*)). After that, procedures from step 2-3 are repeated.

(Step 2-5 in FIG. 2)

If the distance between the tip of the pipette 4 and the sample 3 is within the control value, the pipette 4 is made to vibrate by the control section 7 and the vibration section 5 (refer to FIG. 3(*b*)). At this time, the range of a parameter for vibrating the pipette 4 is stored in advance in the ROM 82. Specifically, the control section 7 sweeps parameters for vibrating the pipette 4 in a predetermined range.

In doing so, one of the parameters will cause the sample 3 to be drawn towards the pipette 4.

(Steps 2-6 and 2-7 in FIG. 2)

If the distance between the sample 3 and the tip of the pipette 4 approaches a specified distance due to the operation of step 2-5 (step 2-6), then a parameter for reproducing a vibrating wave that caused that movement (this vibrating wave is equivalent to a first vibrating wave) is stored in the RAM 82 of the storage section 8. The determination of step 2-6 is carried out by the control section 7 based on the image of the camera 10. The parameter for reproducing this first vibrating wave is, for example, vibration frequency and amplitude, but can also further include other information. The specified distance used in the determination of step 2-6 is also stored in advance in the ROM 81

As a result of this operation, it is possible to automatically acquire a parameter for bringing the sample 3 close to the pipette 4.

(Step 2-8 in FIG. 2)

Next, the control section 7 determines whether or not the sample 3 has stopped at a specified position, based on an image acquired by the camera 10. This specified position is also stored in advance in the ROM 81. If the result of determination is "no", movement (approach) operations of the sample 3 continue. If the result of determination is "yes", processing advances to the next step 2-9. If the result of decision is "no", step 2-8 is repeated for a specified time. If movement does not stop within a prescribed time, an error is generated.

(Step 2-9 in FIG. 2)

Next, the vibration parameter is changed by the control section 7. This parameter after change is also stored in advance in the ROM 81.

Next, the pipette 4 is again vibrated by the vibration section 5, based on the parameter after change (refer to FIG. 3(*c*)). Specifically, the control section 7 sweeps parameters for vibrating the pipette 4 in a range after change.

In doing this, one of the parameters will rotate the sample 3 and change the angle of the sample 3.

(Steps 2-10 and 2-11 in FIG. 2)

If the pipette 4 is rotated by a specified angle due to the operation of step 2-9, then a parameter for reproducing a vibrating wave that caused that movement (this vibrating wave is equivalent to a second vibrating wave) is stored in the RAM 82 of the storage section 8. The determination of step 2-10 is also carried out by the control section 7 based on the image acquired by the camera 10. The parameter for reproducing this second vibrating wave is, for example, vibration frequency and amplitude, but can also further include other information. The specified angle used in the determination of step 2-10 is also stored in advance in the ROM 81. In the event that the pipette 4 is not rotated by the specified angle, vibration continues with the parameter either kept as it is or changed.

As a result of this operation, it is possible to automatically acquire a parameter for rotating the sample 3 by a specified angle. If rotation is not achieved within a prescribed time, an error is determined and operation terminates.

(Method of Controlling Sample Movement, Using the Device of this Embodiment)

Next, a method for controlling sample movement, using the device of this embodiment, will be described with reference to FIG. 4.

Figure 4:
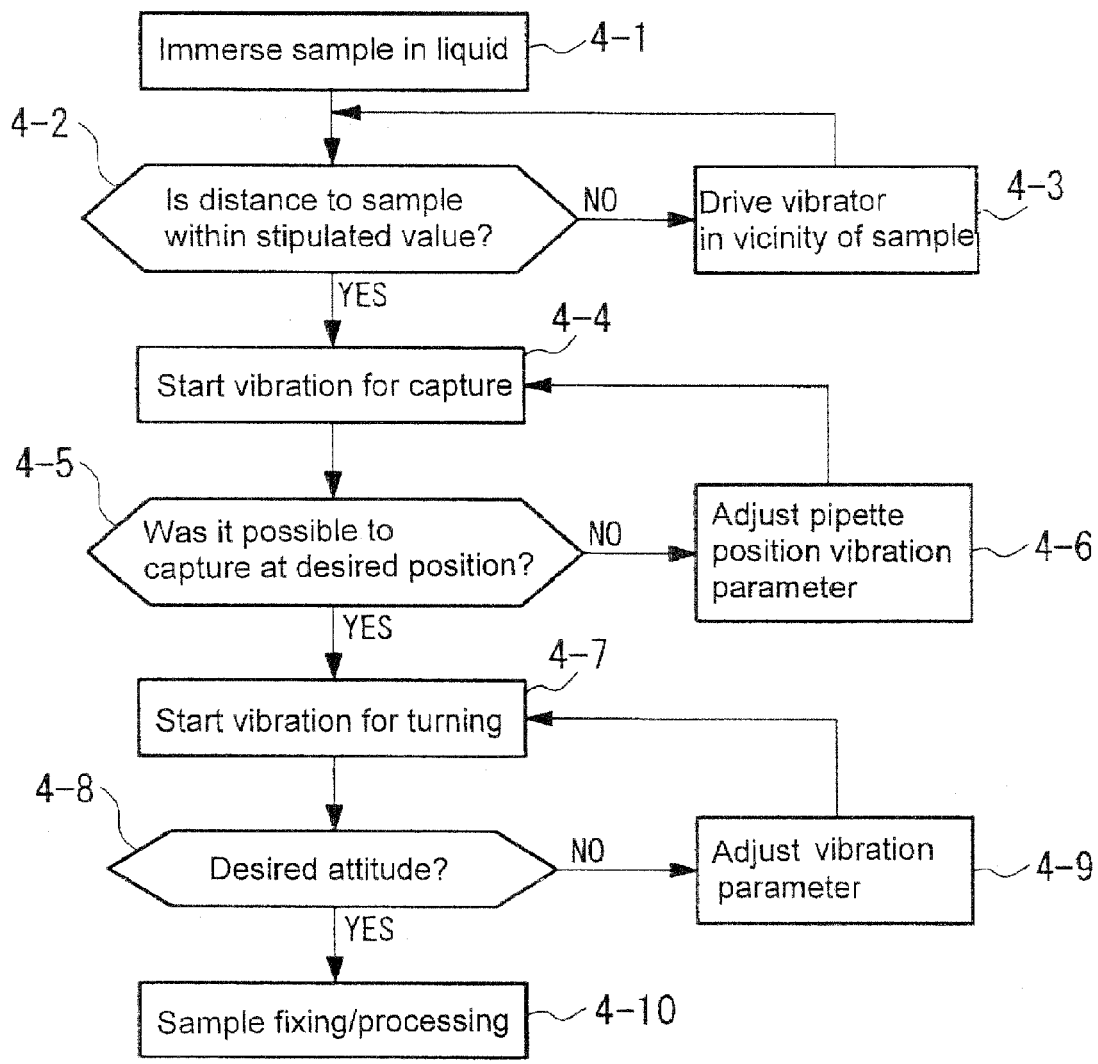
FIG. 4 is a flowchart for describing a method of controlling sample manipulation, using the device of FIG. 1.

(Step 4-1 in FIG. 4)

The sample 3 is first placed in the liquid 2. An image including the tip of the pipette 4 and the sample 3 is then acquired by the camera 10. This image is then analyzed, positions of the pipette tip and the sample are analyzed by the control section 7, and the results are stored in the RAM 82 of the storage section 8.

(Step 4-2 in FIG. 4)

Next, it is determined by the control section 7 whether or not the distance between the tip of the pipette 4 and the sample 3 is within a control value. The control value is stored in advance in the ROM 81. If the determination is "no", processing advances to step 4-3, while if the determination is "yes" processing advances to step 4-4.

(Step 4-3 in FIG. 4)

Figure 5:
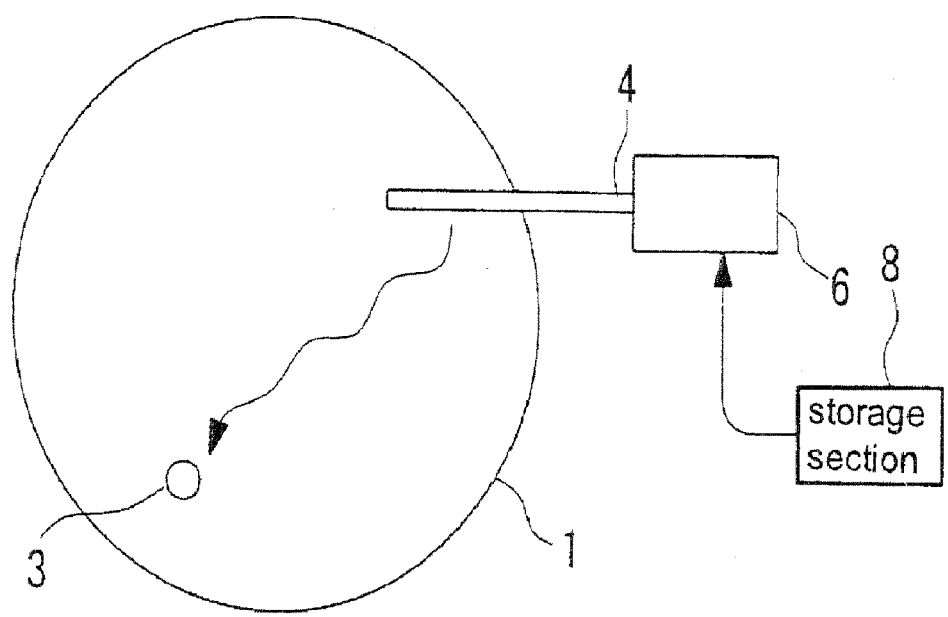
FIG. 5 is an explanatory drawing for describing operation of the device of FIG. 1 in controlling sample manipulation.

Next, the robot 6 is moved by the control section 7, and the tip of the pipette 4 approaches the sample 3 (refer to FIG. 5). After that, the determination of step 4-2 and subsequent operations are performed again.

(Step 4-4 in FIG. 4)

If the determination in step 4-2 is yes, that is, if the distance between the tip of the pipette 4 and the sample 3 is within a control value, the control section 7 generates vibration signals based in parameters stored in the storage section 8 (parameters for generating the first vibrating wave), and sends these signals to the vibration section 5. The vibration section 5 generates a first vibrating wave, and wave motion is caused in the liquid 2 based on this vibrating wave to vibrate the pipette 4. Here, the first vibrating wave causes the sample 3 to be closer to the pipette 4, as described previously.

Accordingly, according to this embodiment it is possible to perform manipulation so as to bring the sample 3 close to the pipette 4 using vibration.

(Steps 4-5 and 4-6 in FIG. 4)

It is next determined by the control section 7 whether or not the sample 3 is at a specified position. This determination can be carried out based on an image acquired by the camera 10.

If the result of determination here is "no", a vibration parameter of the pipette 4 is manually or automatically changed and vibration is performed based on the parameter after change (step 4-4). After that processing again advances to step 4-5.

If the determination n step 4-5 is "yes", processing advances to step 4-7.

(Step 4-7 in FIG. 4)

The control section 7 then generates vibration signals based on another parameter stored in the storage section 8 (parameter for generating a second vibrating wave), and these vibration signals are sent to the vibration section 5. The vibration section 5 generates a second vibration wave, and the pipette 4 is caused to vibrate based on this vibration. The second vibrating wave causes the sample 3 to rotate, as described previously.

It therefore becomes possible to rotate the sample 3 with this embodiment. Also, by adjusting the vibration time, it is also possible to carry out an operation to rotate the sample 3 by a specified angle.

(Step 4-8 in FIG. 4)

Next, the control section 7 determines whether or not the sample 3 is at a specified angle (attitude). This specified angle is also stored in advance in the ROM 81. This determination can also be carried out based on an image acquired by the camera 10.

(Step 4-9 in FIG. 4)

If the result of determination in step 4-8 is "no", a vibration parameter of the pipette 4 is manually or automatically changed, vibration is performed based on the parameter after change (step 4-7), and processing again advances to step 4-8.

(Step 4-10 in FIG. 4)

If the determination in step 4-8 is "yes", the sample 3 is fixed at that position, and the processing required for the sample 3 is performed. The procedure for fixing the sample is the same as in the related art.

EXAMPLE 1

Figure 6:
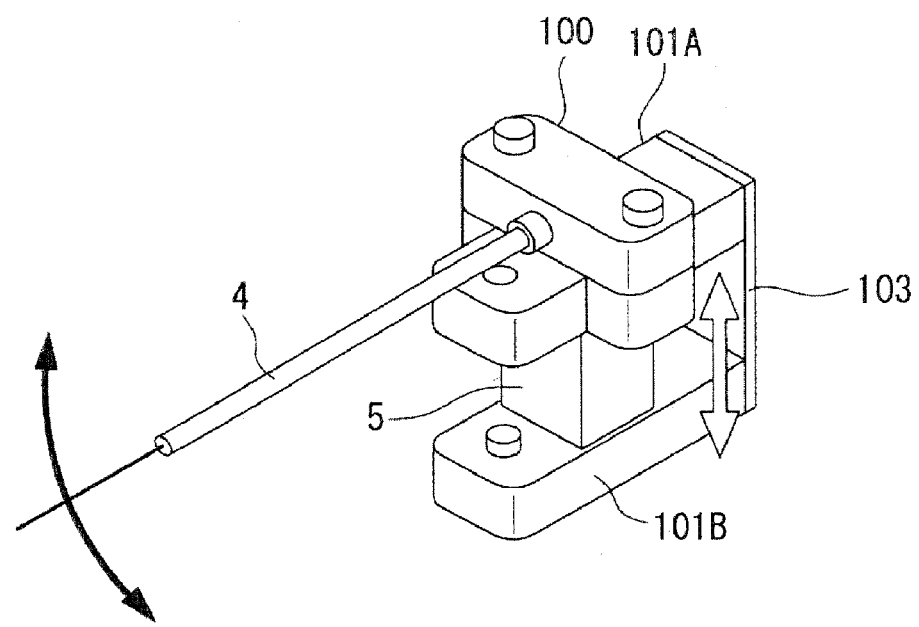
FIG. 6 is an explanatory drawing showing a specific structure of a pipette and vibration section of a first example of the present invention.

One example of a specific structure of the vibration section will now be described. In FIG. 6, the pipette (specifically, a holding pipette) 4 is mounted in a pipette attachment fixture 100, and this pipette attachment fixture 100 is held in a base 101A. This base 101A is attached to another base 101B by means of the vibration section 5, which is a piezoelectric element. The base 101A and the base 101B are further fixed in a cantilevered state by a resilient member, for example, a phosphor bronze plate.

Figure 7:
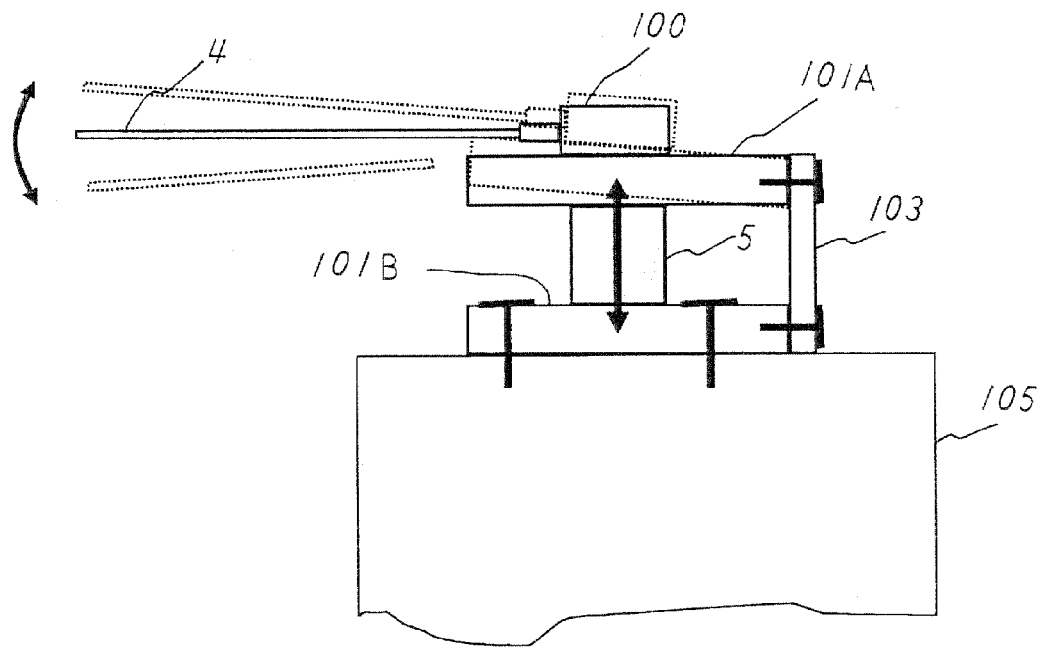
FIG. 7 is a side view of FIG. 6.

In this state, as shown in FIG. 7, the pipette 4 vibrates through a very small arc. The base 101B is attached to a robot 6 (not shown) that is capable of movement in the X, Y and θ directions via an arm 105.

As one example, a design applicable to the case of capture of an ovum will be described. The diameter of a human ovum is about 100 μm, and in capturing this ovum (the specific gravity is substantially the same as that of water), a pipette 4 having a tip outer diameter of 100 μm and an inner diameter of 15 μm is prepared. A vibration frequency of 100-190 Hz can be considered appropriate for the pipette 4. In setting the range, it is considered preferable for amplitude of vibration for driving the pipette 4 to be 20-28 μm, and thickness of the piezoelectric element 102 to be 10 mm. In this case, it can be considered to hold the tip of the pipette 4 at a vibration amplitude of 20-28 μm.

EXAMPLE 2

Movement of the sample described in FIG. 3 for the previously described embodiment will be more specifically described with reference to FIG. 8. With this example 2, an ovum is used as the sample. If the pipette 4 is moved to a range P where the sample (ovum) 3 can be captured, the sample 3 is moved by vibration of the pipette 3 from the position B of the container 1 (dish) to position C so as to be closer to the pipette 4, and ultimately drawn to position D. Continuing on, the sample 3 is subjected to rotational movement as described in the previous example.

Incidentally, the position A is a position outside of the range where the pipette 4 can capture the sample 3. In the case where the sample 3 is at this position, the robot 6 is moved to position the pipette 4 at a position in the range where it can capture the sample 3.

Figure 8:
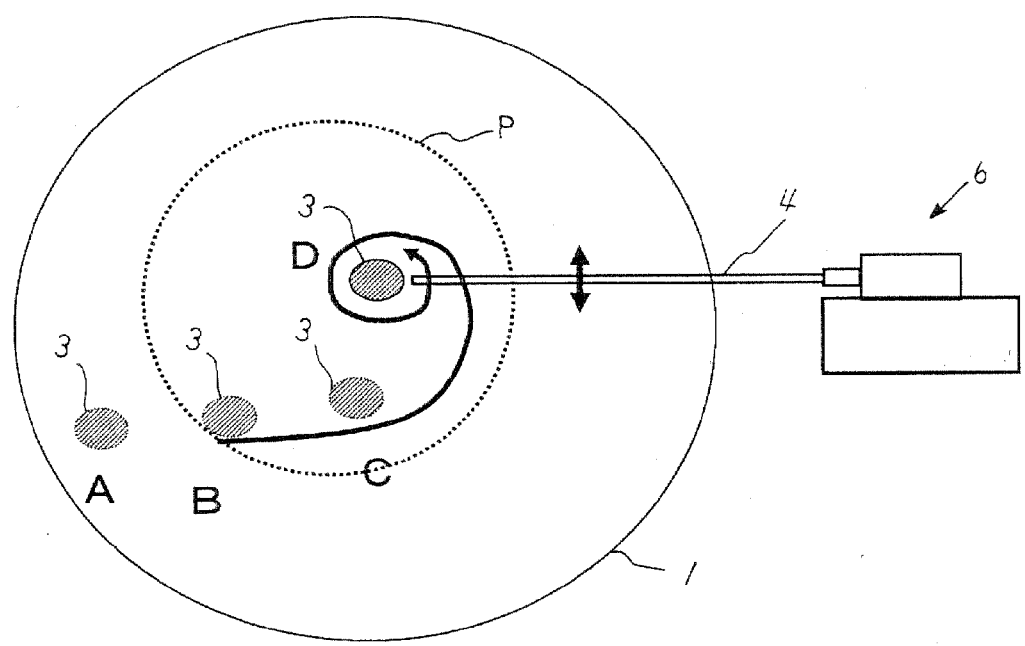
FIG. 8 is an explanatory drawing for describing movement of a sample of a second example of the present invention.

One example of flow of liquid 2 occurring in the processing described in FIG. 8 is shown in FIG. 9(A) and FIG. 9(B). FIG. 9(A) shows flow of the liquid 2 in a state where the pipette 4 is being vibrated in order to bring the sample 3 closer. FIG. 9(B) shows flow of the liquid 2 in a state where the sample 3 is close to the pipette 4 and immediately before it is to be rotated.

As will be understood from the above description, according to the device and method of this embodiment it is possible to simply control position and attitude of a sample, without the need for an expensive device.

With the above-described patent publication 2 (international patent No. WO01/072951), by imparting vibration to generate a standing wave having at least one node to the pipette, water flow is created in the liquid, and the sample is attracted to a nodal part of the pipette. If this is done, there is a limitation on the type of pipette that can be used, and there is a disadvantage such as the position where the sample can be manipulated being limited.

Conversely, with this embodiment, by moving the pipette tip arbitrary flow is created in the liquid in the container, and the sample can be grasped and rotated utilizing this flow. This vibration can be of low amplitude and intermittent. That is, with this embodiment the limitation on types of pipette that can be used is reduced, and it is possible to use various types of pipette as required. Further, with this embodiment the restriction on position for capturing the sample and position for rotating the sample is not limited to a nodal position, as it is with the above described patent publication 2. Also with this embodiment, since there is no need to generate standing waves, the limitation with respect to imparted vibration is reduced. Accordingly, with this embodiment there is the advantage that positional and attitude control of a sample is made easy.

The device and method of the present invention are not limited to the above described embodiment, and it is possible to add various modifications within the scope without departing from the gist of the present invention.

For example, it is also possible for each structural element described above to exist as functional blocks, or to exist as independent hardware. Also, as a method of implementation, it is possible to use hardware or to use computer software. Further, it is possible to implement one functional element of the present invention using a combination of a plurality of functional elements, or to implement a plurality of functional elements of the present invention as a single functional element.

It is also possible for functional elements to be arranged at physically separate positions. In this case, it is also possible to connect functional elements using a network.

The invention claimed is:

1. A sample movement control device, comprising a pipette, a vibration section, a control section, and a storage sections, wherein:
   at least part of the pipette is to be disposed in a liquid;
   the vibrating section is constructed to vibrate the pipette;
   the control section is constructed to supply vibration signals for causing the pipette to vibrate to the vibration section;
   the storage section is constructed to store parameters for generating the vibration signals; and
   the parameters include information for generating a first vibrating wave causing a wave motion for drawing a sample toward a tip of the pipette when the sample exists within a specified distance from the pipette to occur within the liquid, and information for generating a second vibrating wave causing a wave motion for rotating the drawn sample in the vicinity of the tip of the pipette to occur.

2. The sample movement control device of claim 1, wherein information for generating the first vibrating wave and information for generating the second vibrating wave contain at least information on amplitude and frequency of vibration, and wherein neither of the first vibrating wave and the second vibrating wave is a standing wave.

3. The sample movement control device of claim 1, wherein a piezoelectric element is used as the vibration section.

4. The sample movement control device of claim 3, wherein the pipette is attached to a vibration section, and the vibration section is attached to a robot for moving in at least the X and Y directions.

5. A method for acquiring a parameter for sample manipulation, comprising:
   (1) a step of storing pipette position and sample position in a storage section;
   (2) a step of, after step (1), determining, using a control section, whether or not a distance between a tip of a pipette and a sample is within a specified range;
   (3) a step of storing, when the distance between the tip of the pipette and the sample is within a specified distance, a parameter for causing the pipette to vibrate so as to reproduce a first vibrating wave at the time the sample has moved close to the tip of the pipette; and
   (4) a step of, after step (3), storing a parameter for causing the pipette to vibrate so as to reproduce a second vibrating wave at the time the sample has been rotated in the vicinity of the tip of the pipette.

6. A method for controlling sample manipulation, comprising:
   (1) a step of storing pipette position and sample position in a storage section;
   (2) a step of, after step (1), determining, using a control section, whether or not a distance between a tip of a pipette and a sample is within a specified range;
   (3) a step of generating a first vibrating wave based on a parameter stored in a storage section when the distance between the tip of the pipette and the sample is within a specified distance and causing the sample to move close to the tip of the pipette; and
   (4) a step of, after step (3), generating a second vibrating wave based on a parameter stored in the storage section, to cause the pipette to vibrate, and causing the sample to rotate in the vicinity of the tip of the pipette.

7. A method for acquiring a parameter for sample manipulation, comprising:
   (1) a step of determining, using a control section, whether or not a distance between a tip of a pipette and a sample is within a specified range;
   (2) a step of storing, when the distance between the tip of the pipette and the sample is within a specified distance, a parameter for causing the pipette to vibrate so as to reproduce a first vibrating wave at the time the sample has moved close to the tip of the pipette; and
   (3) a step of, after step (2), storing a parameter for causing the pipette to vibrate so as to reproduce a second vibrating wave at the time the sample has been rotated in the vicinity of the tip of the pipette.

8. A method for controlling sample manipulation, comprising:
   (1) a step of determining, using a control section, whether or not a distance between a tip of a pipette and a sample is within a specified range;
   (2) a step of generating a first vibrating wave based on a parameter stored in a storage section when the distance between the tip of the pipette and the sample is within a specified distance to cause the pipette to vibrate, and causing the sample to move close to the tip of the pipette; and
   (3) a step of, after step (2), generating a second vibrating wave based on a parameter stored in the storage section, to cause the pipette to vibrate, and causing the sample to rotate in the vicinity of the tip of the pipette.

* * * * *

UNITED STATES PATENT AND TRADEMARK OFFICE
CERTIFICATE OF CORRECTION

| | |
|---|---|
| PATENT NO. | : 7,726,210 B2 |
| APPLICATION NO. | : 11/573871 |
| DATED | : June 1, 2010 |
| INVENTOR(S) | : O. Fuchiwaki et al. |

Page 1 of 1

It is certified that error appears in the above-identified patent and that said Letters Patent is hereby corrected as shown below:

| COLUMN | LINE | ERROR |
|---|---|---|
| 9 (Claim 1, line 3) | 42 | "sections" should read --section-- |

Signed and Sealed this

Twenty-third Day of November, 2010

David J. Kappos
*Director of the United States Patent and Trademark Office*